US011395640B2

(12) United States Patent
Pelissier et al.

(10) Patent No.: US 11,395,640 B2
(45) Date of Patent: *Jul. 26, 2022

(54) SYSTEM AND METHOD FOR LOCATING AN ULTRASOUND IMAGING DEVICE FROM A MULTI-USE ELECTRONIC DISPLAY DEVICE

(71) Applicant: Clarius Mobile Health Corp., Burnaby (CA)

(72) Inventors: Laurent Pelissier, North Vancouver (CA); Trevor Hansen, Vancouver (CA); Kris Dickie, Vancouver (CA)

(73) Assignee: Clarius Mobile Health Corp., Vancouver (CA)

( * ) Notice: Subject to any disclaimer, the term of this patent is extended or adjusted under 35 U.S.C. 154(b) by 761 days.

This patent is subject to a terminal disclaimer.

(21) Appl. No.: 16/198,847

(22) Filed: Nov. 22, 2018

(65) Prior Publication Data

US 2019/0090848 A1    Mar. 28, 2019

Related U.S. Application Data

(63) Continuation of application No. 15/663,583, filed on Jul. 28, 2017, now Pat. No. 10,159,465, which is a
(Continued)

(51) Int. Cl.
*A61B 8/00* (2006.01)
*G16H 30/20* (2018.01)
(Continued)

(52) U.S. Cl.
CPC ........... *A61B 8/465* (2013.01); *A61B 8/4427* (2013.01); *A61B 8/4472* (2013.01);
(Continued)

(58) Field of Classification Search
CPC ..... A61B 8/465; A61B 8/4477; A61B 8/4427; A61B 8/461; A61B 8/4472; A61B 8/565;
(Continued)

(56) References Cited

U.S. PATENT DOCUMENTS 6,142,946 A    11/2000 Hwang et al.
6,475,146 B1   11/2002 Frelburger et al.
(Continued)

FOREIGN PATENT DOCUMENTS

CA    2979920 C    6/2018
EP    2805677 A1   11/2014
(Continued)

OTHER PUBLICATIONS

Response dated May 24, 2019 to the European Examination Report of Nov. 21, 2018, for corresponding European Patent Application No. 16771129.0.
(Continued)

*Primary Examiner* — Sanjay Cattungal
(74) *Attorney, Agent, or Firm* — Julian Ho

(57) ABSTRACT

An ultrasound imaging system comprising a multi-use electronic display device and an ultrasound imaging device. The multi-use electronic display device is capable of communicating with one or more ultrasound imaging devices and selecting which to connect with based on at least one of previously store information, user input, and information gathered from the ultrasound imaging devices. The multi-use electronic display device may communicate with the ultrasound imaging devices while they are in a low power standby state. This approach reduces the complexity of the pairing process and provides a means for quickly and easily selecting between multiple ultrasound imaging devices.

20 Claims, 8 Drawing Sheets

Related U.S. Application Data continuation of application No. 14/671,773, filed on Mar. 27, 2015, now Pat. No. 9,763,644.

(51) Int. Cl.

| | |
|---|---|
| *G16H 40/67* | (2018.01) |
| *G16H 40/63* | (2018.01) |
| *G16H 40/20* | (2018.01) |
| *G01S 7/52* | (2006.01) |
| *A61B 8/08* | (2006.01) |
| *G16H 50/20* | (2018.01) |

(52) U.S. Cl.
CPC ............ *A61B 8/4477* (2013.01); *A61B 8/461* (2013.01); *A61B 8/54* (2013.01); *A61B 8/565* (2013.01); *G01S 7/52082* (2013.01); *G16H 30/20* (2018.01); *G16H 40/20* (2018.01); *G16H 40/63* (2018.01); *G16H 40/67* (2018.01); *A61B 8/0841* (2013.01); *A61B 8/4245* (2013.01); *A61B 8/4411* (2013.01); *A61B 8/4438* (2013.01); *A61B 8/488* (2013.01); *A61B 8/56* (2013.01); *G01S 7/52096* (2013.01); *G16H 50/20* (2018.01)

(58) Field of Classification Search
CPC ....... A61B 8/54; A61B 8/4411; A61B 8/4438; A61B 8/56; A61B 8/4245; A61B 8/488; A61B 8/0841; G01S 7/52082; G01S 7/52096; G16H 40/20; G16H 40/63; G16H 30/20; G16H 40/67; G16H 50/20
See application file for complete search history.

(56) References Cited

U.S. PATENT DOCUMENTS

| | | | |
|---|---|---|---|
| 6,780,154 B2 | 8/2004 | Hunt et al. | |
| 7,507,204 B2* | 3/2009 | Shim | A61B 8/483 600/443 |
| 8,461,978 B2 | 6/2013 | Garner et al. | |
| 9,763,644 B2 | 9/2017 | Pelissier et al. | |
| 10,159,465 B2 | 12/2018 | Pelissier et al. | |
| 2005/0124890 A1 | 6/2005 | Halmann et al. | |
| 2007/0083111 A1 | 4/2007 | Hossack et al. | |
| 2007/0255136 A1* | 11/2007 | Kristofferson | A61B 8/5223 600/437 |
| 2009/0112099 A1 | 4/2009 | Kurokawa | |
| 2009/0306503 A1* | 12/2009 | Srinivasan | A61B 8/00 600/441 |
| 2010/0191121 A1 | 7/2010 | Satoh et al. | |
| 2010/0277305 A1* | 11/2010 | Garner | A61B 8/4438 340/539.1 |
| 2011/0105904 A1 | 5/2011 | Watanabe | |
| 2012/0213136 A1 | 8/2012 | Woo et al. | |
| 2012/0214417 A1 | 8/2012 | Woo et al. | |
| 2013/0028153 A1 | 1/2013 | Kim et al. | |
| 2013/0150718 A1* | 6/2013 | Dixon | A61B 8/483 600/443 |
| 2013/0150719 A1* | 6/2013 | Orderud | A61B 8/483 600/443 |
| 2013/0184587 A1 | 7/2013 | Eom et al. | |
| 2013/0190624 A1 | 7/2013 | Beger et al. | |
| 2013/0226001 A1 | 8/2013 | Steen et al. | |
| 2014/0180110 A1 | 6/2014 | Schmedling | |
| 2014/0308898 A1 | 10/2014 | Lee et al. | |
| 2014/0323869 A1 | 10/2014 | Jin et al. | |
| 2015/0065882 A1 | 3/2015 | Cho et al. | |
| 2015/0238168 A1 | 8/2015 | Poland | |
| 2016/0120507 A1 | 5/2016 | Ninomiya et al. | |
| 2016/0278739 A1 | 9/2016 | Pelissier et al. | |

FOREIGN PATENT DOCUMENTS

| | | |
|---|---|---|
| JP | 6732879 | 7/2020 |
| WO | 2016154739 A1 | 10/2016 |

OTHER PUBLICATIONS

European Examination Report dated Apr. 15, 2021 for corresponding European Patent Application No. 16771129.0.
Healcerion Sonon 300C User Manual Rev. 2, retrieved Feb. 27, 2015.
Agarwal et al., "Dynamic power management using on demand paging for networked embedded systems", Proceedings of the ASP-DAC 2005, Asia and South Pacific Design Automation Conference, 2005, vol. 2, pp. 775-759, Jan. 18-21, 2005 (Jan. 18, 2005).
International Search Report and Written Opinion of the International Searching Authority for corresponding PCT International Application No. PCT/CA2016/050343 filed Mar. 23, 2016.
"Find Me Profile", Bluetooth Profile Specification, prepared by PUID WG, Jun. 21, 2011, FMP_SPEC, Revision V10r00.
"Proximity Profile", Bluetooth Specification, prepared by PUID WG, Jun. 21, 2011, PXP_SPEC, Revision V10r00.
"TX Power Service", Bluetooth Specification, prepared by PUID WG, Jun. 21, 2011, TPS_SPEC, Revision V10r00.
Extended European Search Report from the European Patent Office, dated Nov. 21, 2018, for corresponding European patent application 16771129.0.
Canadian Office Action dated Oct. 18, 2017, from the Canadian Intellectual Property Office, for corresponding Canadian Patent Application No. 2,979,920, now issued as Canadian Patent 2,979,920.
Office Action Response (not including the attachments) dated Jan. 16, 2018 to the Canadian Office Action dated Oct. 18, 2017, for corresponding Canadian Patent Application No. 2,979,920, now issued as Canadian Patent 2,979,920.
Canadian Office Action dated Jan. 30, 2018, from the Canadian Intellectual Property Office, for corresponding Canadian Patent Application No. 2,979,920, now issued as Canadian Patent 2,979,920.
Office Action Response (not including the attachments) dated Mar. 28, 2018 to the Canadian Office Action dated Jan. 30, 2018, for corresponding Canadian Patent Application No. 2,979,920, now issued as Canadian Patent 2,979,920.

* cited by examiner

SYSTEM AND METHOD FOR LOCATING AN ULTRASOUND IMAGING DEVICE FROM A MULTI-USE ELECTRONIC DISPLAY DEVICE

CROSS-REFERENCE TO RELATED APPLICATIONS

This application is a continuation of U.S. patent application Ser. No. 15/663,583, filed Jul. 28, 2017, which is a continuation of U.S. patent application Ser. No. 14/671,773, filed Mar. 27, 2015. U.S. patent application Ser. No. 14/671,773 issued to patent as U.S. Pat. No. 9,763,644. The entire contents of U.S. patent application Ser. No. 14/671,773 and U.S. patent application Ser. No. 15/663,583 are hereby incorporated by reference.

FIELD

This invention generally relates to ultrasound imaging systems. In particular, the invention relates to ultrasound imaging systems comprising an ultrasound imaging apparatus and a multi-use electronic display device, and to methods for communication between ultrasound imaging apparatus and multi-use display devices.

BACKGROUND

Ultrasound imaging systems are an important tool for diagnosis and therapy in a wide range of medical applications. Conventionally, ultrasound systems were large, expensive units used only in radiology departments by highly trained specialists. To improve portability and usability and enable ultrasound to be used at the point-of-care and by more users, various attempts have been made to reduce the size and cost of these systems and avoid the ergonomically troublesome cables that are typically used to attach handheld transducers to processing hardware.

For example, U.S. Pat. No. 6,780,154 discloses a handheld medical diagnostic ultrasound imaging system that wirelessly communicates ultrasound data to a multi-use display device such as a commercially available PDA or tablet computer.

In addition to size and cost, wireless ultrasound systems may also face challenges related to bandwidth and power. A high bandwidth is desirable in order to support high quality images and high frame rates. However, high bandwidth wireless connections typically have high power consumption, which can quickly drain the battery of a wireless imaging device.

Some applications, like emergency medicine, may be time-critical. In such applications, users may need to begin imaging without delay. Some ultrasound systems can take a long time, on the order of 30-45 seconds, to boot up. It may not be practical for a battery-powered device to remain on when not in use. Wireless communication links generally require some sort of initialization procedure in order to establish communication. This pairing process can take a long time and be prone to errors, further delaying the start of imaging.

There remains a need for wireless ultrasound imaging systems that enable users of multi-use display devices to connect to ultrasound imaging devices quickly, easily, and securely. There is a particular need for such systems that provide multiple ultrasound imaging devices and allow users to rapidly select and commence imaging using a selected one of the ultrasound imaging devices.

SUMMARY

The description of the invention which follows, together with the accompanying drawings should not be construed as limiting the invention to the examples shown and described, because those skilled in the art to which this invention pertains will be able to devise other forms thereof within the scope of the appended claims.

In accordance with one or more embodiments, a wireless ultrasound imaging system comprises a multi-use display device and an ultrasound imaging device. The multi-use display device is configured to acquire ultrasound imaging device selection data from one or more ultrasound imaging devices, select an ultrasound imaging device, direct the selected ultrasound imaging device to acquire ultrasound data, receive the ultrasound data from the selected ultrasound imaging device and display the ultrasound data.

One aspect provides an ultrasound imaging method. The method comprises, by a multi-use electronic display device: using a first wireless communication protocol to acquire imaging device selection information from each of one or more ultrasound imaging devices. The method selects one of the one or more ultrasound imaging devices for use in an ultrasound procedure based on the selection information. The method then establishes a primary wireless communication link with the selected one of the ultrasound imaging devices according to a second wireless communication protocol different from the first wireless communication protocol. The method commands the selected one of the ultrasound imaging devices to acquire ultrasound image data. Subsequently, the method receives the ultrasound image data by way of the primary wireless communication link; and displays the received ultrasound image data on a screen of the multi-use electronic display device. The first wireless communication protocol may, for example, comprise a Bluetooth protocol.

In some embodiments the method comprises, by the multi-use electronic display device: determining from the selection information a controllable function of the ultrasound imaging device; and in response to determining the controllable function, configuring the multi-use electronic display device to provide at least one user interface control for the controllable function.

In some embodiments the selection information comprises link information for each of the one or more ultrasound imaging devices and establishing the primary wireless communication link with the selected one of the ultrasound imaging devices comprises using the link information to establish data communication between the multi-use display device and the selected ultrasound imaging device according to the second wireless data communication protocol. The link information may include, for example an address, name, ID or other information identifying the selected ultrasound imaging device. The link information may optionally include other information useful for setting up the primary wireless communication link such as encryption keys or other encryption information, protocol information, etc.

In some embodiments the selection information comprises battery charge information indicative of a state of charge of batteries of the ultrasound imaging devices. In some embodiments the first wireless communication protocol is a protocol that does not require the ultrasound imaging devices to be powered. For example, the first wireless communication protocol may comprise an RFID protocol. In some embodiments the method comprise, at the multi-use electronic display device, determining the ultrasound procedure to perform on a patient and selecting one of the one or more ultrasound imaging devices comprises limiting the selection to those of the ultrasound imaging devices that possess an adaptation necessary for the ultrasound procedure. The adaptation may comprise, for example one or more of, a Doppler imaging mode or other special imaging mode; a transducer having a configuration required for the determined ultrasound procedure; a needle guide or other structural adaptation; a data transceiver providing a desired bandwidth, etc.

In some embodiments selecting one of the one or more ultrasound imaging devices comprises a filtering stage in which those of the ultrasound imaging devices potentially suitable for the ultrasound procedure are identified and a selection stage comprising, if more than one of the ultrasound imaging devices are potentially suitable for the procedure, selecting one of the more than one of the ultrasound imaging devices that are potentially suitable for the procedure.

In some embodiments acquiring imaging device selection information from each of one or more ultrasound imaging devices is performed while some or all of the ultrasound imaging devices are in a low-power standby state and the method comprises commanding the selected one of the ultrasound imaging devices to switch to an active or power on state.

In some embodiments, the method comprises, by way of the first wireless communication protocol commanding the selected one of the ultrasound imaging devices to issue a human-perceptible visual or audible signal. The visual or audible signal may be used to locate the selected ultrasound imaging device or to distinguish the selected ultrasound imaging device from other similar-looking ultrasound imaging devices. In some embodiments the method comprises, before selecting one of the one or more ultrasound imaging devices, displaying at the multi-use display device at least some of the selection information for each of a plurality of the ultrasound imaging devices, the displayed selection information including one or more of: type of an ultrasound transducer type of the ultrasound imaging device; nickname of the ultrasound imaging device; battery state of charge of the ultrasound imaging device; and strength of signals in the first wireless communication protocol received at the multi-use display device from the ultrasound imaging device.

The above-noted features may be combined in any combinations and sub-combinations to yield various non-limiting example embodiments.

Another aspect provides an ultrasound imaging system comprising an ultrasonic imaging apparatus which wirelessly communicates with a multi-use electronic display device for display of ultrasound image data acquired by the ultrasonic imaging device. The ultrasonic imaging apparatus comprises: an imaging unit operable to transmit ultrasound energy and acquire ultrasound data; a processor, coupled to and configured to control the imaging unit; a pairing unit, coupled to the processor and configured to establish a preliminary data connection with the multi-use electronic display device; a communication unit, coupled to the processor and configured to communicate ultrasound image data to the multi-use electronic display device. The processor is coupled to the first communication interface, imaging unit, and pairing unit and is operable to receive imaging configuration data from the multi-use electronic display device. The multi-use electronic display device comprises: an external interface configured to communicate with the communication interface and receive said transmitted ultrasound image data information, a second processor, configured to convert said ultrasound image data information into an ultrasound image, a memory, coupled to said second processor; and a user interface, coupled to the second processor and operable to display the ultrasound image.

In some embodiments the external interface comprises first and second wireless transceivers and the communication unit comprises a third wireless transceiver, configured to form a first data connection with the first wireless transceiver; and a fourth wireless transceiver, configured to form a second data connection with the second wireless transceiver. The first and second wireless transceivers may operate according to distinct communication protocols. In some embodiments, information for setting up said second data connection is communicated via the first data connection. In an example embodiment the first wireless transceiver is provided by a Bluetooth module. In the example embodiment the second wireless transceiver may be provided by a Wi-Fi module.

In some embodiments the ultrasound imaging device comprises a sensing unit. The sending unit may, for example, comprise one or more of an inertial measurement unit and a global positioning sensor. One or both of the ultrasound imaging device and multiuse display device may be battery powered portable devices.

In some embodiments, commanding the selected one of the ultrasound imaging devices to acquire ultrasound image data comprises transmitting imaging parameters to the selected one of the ultrasound imaging devices and the method comprises automatically establishing initial values for the imaging parameters at the multi-use imaging device based on the ultrasound procedure.

Another aspect of the invention provides a diagnostic ultrasound imaging system. The diagnostic ultrasound imaging system according to this aspect comprises a multi-use display device operable to wirelessly connect with at least one ultrasound imaging device. The multi-use display device may comprise an off-the-shelf device such as a smart phone, tablet computer, personal digital assistant (PDA) or portable computer configured with software (e.g. an app) which provides functions for establishing a data connection to an ultrasound imaging device, receiving ultrasound image data from the ultrasound imaging device and displaying an ultrasound image on a display of the multi-use display device. The multi-use display device may be operable for uses other than ultrasound imaging.

The multi-use display device comprises a processor, a user interface, a memory, and an external interface. The multi-use display device is operable to wirelessly communicate with the ultrasound imaging device through the external interface to configure imaging parameters and receive ultrasound data.

In some embodiments, the external interface of the multi-use display device may comprise one or more wireless transceivers that provide wireless communications with other devices using a plurality of different wireless communication protocols.

In an example embodiment the ultrasound imaging device comprises a processor, an imaging unit, a pairing unit, a memory, and a communication unit operable to connect with the multi-use display device.

In some embodiments, the ultrasound imaging device may further comprise a sensing unit to generate ultrasound imaging device selection information on the current state of the ultrasound imaging device.

In some embodiments, the ultrasound imaging device may operate in at least a standby state and an active state. The ultrasound imaging device may consume less power in the standby state.

In some embodiments, the ultrasound imaging device is a handheld or hand-carried system. The ultrasound imaging device may be a laptop or cart-based system in the alternative.

Another aspect of the present invention provides a method for using a multi-use display device to wirelessly control and receive data from an ultrasound imaging device. The method comprises: acquiring ultrasound imaging device selection information from one or more ultrasound imaging devices, selecting an ultrasound imaging device based on the plurality of ultrasound imaging device selection information, establishing communication with the selected ultrasound imaging device, directing the selected ultrasound imaging device to acquire ultrasound data, receiving the acquired ultrasound data from the ultrasound imaging device, and displaying the ultrasound data acquired by the ultrasound imaging device on the multi-use display device.

In some embodiments, the ultrasound imaging device selection information may comprise at least one of the following: information gathered from one or more available ultrasound imaging devices, information from the user, and previously stored information.

In some embodiments, the plurality of ultrasound imaging device selection information from one or more ultrasound imaging devices may be acquired while one or more of the ultrasound imaging devices are in a standby state. A selected one of the ultrasound imaging devices may subsequently be transitioned from a standby state to an active state by a user control input or automatically. In some embodiments, the user control input is received at the user interface of a multi-use display device and software on the multi-use display device causes the multi-use display device to transmit a signal to the ultrasound imaging device that causes the ultrasound imaging device to transition to the active state.

In some embodiments, an ultrasound device list may be generated based at least in part on the ultrasound imaging device selection information. This list may also be displayed on multi-use display device 102.

In some embodiments, selecting an ultrasound imaging device may comprise receiving an input from a user via a user interface on the multi-use display device.

In some embodiments, selecting an ultrasound imaging device may comprise an automated step performed by the multi-use display device based on the plurality of pieces of ultrasound imaging device selection information. For example, the multi-use display device may be configured to automatically select the closest ultrasound imaging device, or automatically select the ultrasound imaging device that was previously connected.

Another aspect of the invention provides ultrasound imaging devices as described herein.

Further aspects and example embodiments are illustrated in the accompanying drawings and/or described in the following description.

BRIEF DESCRIPTION OF THE DRAWINGS

The accompanying drawings illustrate non-limiting example embodiments of the invention.

DETAILED DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive sense.

Throughout the following description, a "target object" may be a target inanimate object or a target animate object, which is displayed via an image. Also, the target object may be a part of a human body and may include the liver, the heart, the womb, the brain, the breast, the abdominal region, or the like, a fetus, or a cross-section of a part of the human body. Throughout the following description, a "user" may be a medical expert including a doctor, a nurse, a medical laboratory technologist, a sonographer, or the like.

Figure 1:
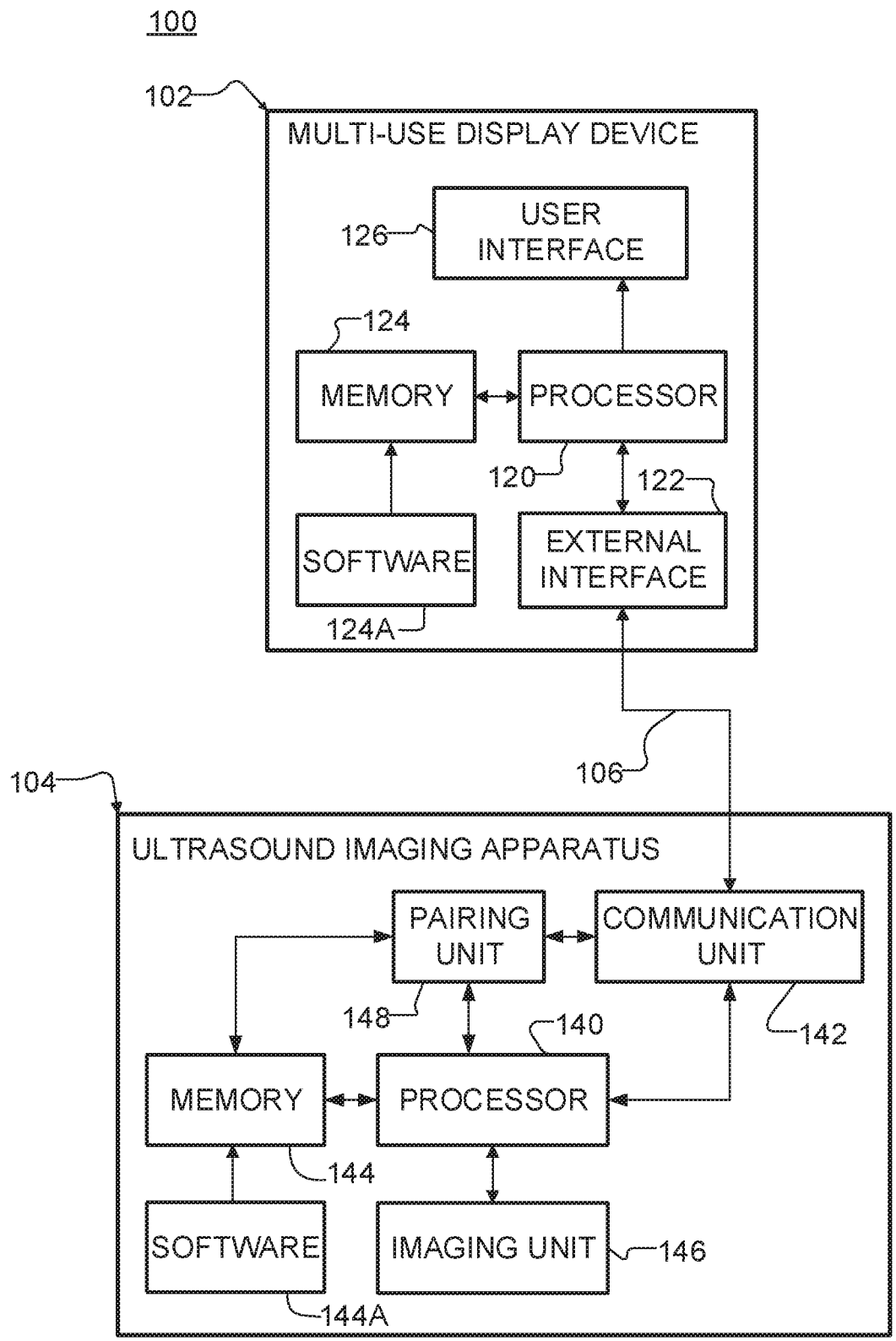
FIG. 1 is a schematic diagram of an ultrasound imaging system according to an example embodiment of the present disclosure.

FIG. 1 is a schematic diagram of an ultrasound imaging system 100 in accordance with an embodiment of the disclosure. Ultrasound imaging system 100 comprises a multiuse display device 102 and an ultrasound imaging device 104.

A communication link 106 between multi-use display device 102 and ultrasound imaging device 104 may be established. Multi-use display device 102 may gather information about ultrasound imaging device 104 by way of link 106. Multi-use display device 102 may establish communication link 106 with one or more other ultrasound imaging devices 104 (not shown in FIG. 1) and may obtain and use information about the ultrasound imaging devices 104 to select among two or more ultrasound imaging devices 104.

Ultrasound imaging device 104 may be wirelessly connected with multi-use display device 102. Ultrasound imaging device 104 may transmit an ultrasound signal to a target object according to a control signal that is transmitted from multi-use display device 102.

Still referring to FIG. 1, multi-use display device 102 may comprise a processor 120, memory 124, user interface 126, and an external interface 122. Processor 120 may be a general purpose CPU or may be a low power/mobile specific processor. Processor 120 is coupled with memory 124. Memory 124 includes storage for program and program operating code. One or more programs 124A in memory 124 coordinates interactions of multi-use display device 102 with ultrasound imaging devices 104 as described herein.

User interface 126 is coupled with processor 120 and may comprise both the software and hardware components necessary to interface with a user of the multi-use display device. User interface 126 may comprise physical input devices such as a touch sensitive display screen, keyboard, microphone, or function buttons. User interface 126 may further comprise output devices such as a color, grayscale, or black and white display screen, audio speaker/output, vibrating or LED indicators.

External interface 122 is coupled with processor 120 and provides connectivity of multi-use display device 102 with ultrasound imaging device(s) 104 though communication link(s) 106. External interface 122 may also be operable to communicate with another device, such as a web server.

Processor 120 may generate control signals to control an operation of ultrasound imaging device 104 according to information that is provided via user interface 126. The control signals may include control signals that control ultrasound imaging device 104 to generate ultrasound signals, and control signals that control how ultrasound imaging device 104 handles transmission and reception of the ultrasound signal. In addition, processor 120 may control wireless communication with ultrasound imaging device 104, and may control generation and display of an ultrasound image on a display of user interface 126 based on ultrasound image data provided from ultrasound imaging device 104.

Still referring to FIG. 1, ultrasound imaging device 104 may comprise a processor 140, memory 144 (storing software 144A), imaging unit 146, pairing unit 148, and a communication unit 142. Processor 140 may comprise a general purpose CPU, a low power/mobile specific processor, a field programmable gate array (FPGA), a combination of two or more of these or the like.

Imaging unit 146 is operable to acquire ultrasound image data of a target object based on control signals from processor 140. Imaging unit 146 may comprise a transmitter for generating ultrasound energy and a receiver for receiving ultrasound energy reflected from the target object. Imaging unit 146 may further comprise an analog-to-digital converter for digitizing the received ultrasound energy into digital ultrasound data. Imaging unit 146 may further comprise one or more beamformers to combine and focus the received ultrasound energy along a desired scanline. Imaging unit 146 may further comprise a signal processor to apply filtering or compression to the ultrasound image data. Imaging unit 146 may also comprise a scan converter for converting the ultrasound image data into a specific display format.

Processor 120 is coupled with memory 124. Memory 124 includes storage for program and program operating code. One or more programs in memory 124 coordinates the operation of ultrasound imaging device 104 as described herein. Memory 124 may also be used to store information about ultrasound imaging device 104 and/or ultrasound image data.

Pairing unit 148 is operable to establish communication link 106 between communication unit 142 and external interface 122 of multi-use display device 102. Communication unit 142 may comprise one or more wireless transceivers.

In some embodiments, ultrasound imaging device 104 may function in at least a standby state and an active state. In the standby state, some of the internal subsystems of ultrasound imaging device 104 may be powered and thus functional while others are powered down. For example, in the standby state all subsystems may be powered down except for pairing unit 148 and communication unit 142. In the standby state, ultrasound imaging device 102 is able conserve power, which may extend battery life. In the active state, all subsystems of ultrasound imaging device 102 may be powered. Ultrasound imaging devices 104 may be transitioned from a standby state to an active state by activating a control on the ultrasound imaging device 104. Alternatively, ultrasound imaging devices 104 may be transitioned from a standby state to an active state in response to a signal or command received through communication unit 142.

Ultrasound imaging devices 104 may have any of a wide range of various sizes and configurations. For example, ultrasound imaging device 104 may be handheld or hand carried. Alternatively, ultrasound imaging device 104 may be in a laptop form factor or a more traditional cart-based device. In some preferred embodiments, ultrasound imaging devices 104 have the form of hand-held battery-powered probes.

Communication link 106 may comprise more than one communication protocol. In some embodiments, a first protocol is applied for initial discovery of an ultrasound imaging device 104 by multi-use display device 102 as well as acquisition of data useful for selecting the ultrasound imaging device 104 and information useful for establishing a communications link according to a second protocol with the ultrasound imaging device 104. The second protocol may provide a longer range and/or higher bandwidth connection than the first protocol.

For example, a preliminary connection may be a Bluetooth™ low energy (BLE) connection and a primary connection may be a Wi-Fi connection. Alternatively, one or more of the following protocols may be used: wireless local area network (LAN), Bluetooth, ZigBee™, Wi-Fi Direct (WFD), ultra wideband (UWB), infrared data association (IrDA), Bluetooth low energy (BLE), near field communication (NFC), wireless broadband internet (Wibro), world interoperability for microwave access (WiMAX), shared wireless access protocol (SWAP), radio frequency (RF) communications and the like.

Once the desired ultrasound imaging device 104 is selected, the preliminary connection may be operable to setup a primary connection for communication and data transfer between multi-use display device 102 and ultrasound imaging device 104.

In some embodiments, software processes running on multi-use display device 102 play a role in selection of an ultrasound imaging device 104. To give three examples, selection may be based on one or more of: capabilities of the ultrasound imaging device 104; proximity to multi-use display device 102; and rights of a user of multi-use display device 102. Selection may also be based on combinations of two or more of these or other factors with one another.

In a first example, a user selects an ultrasound imaging procedure to perform. Not all of ultrasound imaging devices 104 are suitable for the procedure. Multi-use display device 102 may display for selection only those available ultrasound imaging devices 104 that are suitable for the procedure. This filtering may be based on information regarding the configuration and/or capabilities of the ultrasound imaging devices 104 provided by way of preliminary connections to those devices.

As a second example, multi-use display device 102 determines distance to each of ultrasound imaging devices 104 and sorts a list of available ultrasound imaging devices 104 by distance. Distance may be measured by monitoring signal strength of signals from the ultrasound imaging devices on the preliminary communication channel.

As a third example, different multi-use display devices 102 may have rights to access different ultrasound imaging devices. Some ultrasound imaging devices may be available only to physicians. Others may be available only to members of a certain department. Others may be available only to certain individuals, and so on. Multi-use display device 102 may use information obtained from the preliminary data connection to determine whether it is authorized for use with the ultrasound imaging device 104 and may display for selection only those ultrasound imaging devices 104 for which the multiuse display device 102 is authorized.

In some embodiments, the preliminary protocol is a protocol that does not require the ultrasonic imaging device to be powered. For example, the preliminary protocol may comprise an RFID protocol. An RFID chip on the ultrasonic imaging device 104 may contain information identifying the ultrasonic imaging device 104, describing capabilities of the ultrasonic imaging device 104, and/or describing how to establish a second (primary) data connection to the ultrasonic imaging device 104. In such embodiments, multi-use display device 102 may incorporate an RFID reader or system 100 may include a separate RFID reader with which multi-use display device 102 communicates by a suitable protocol, for example Bluetooth.

Figure 2:
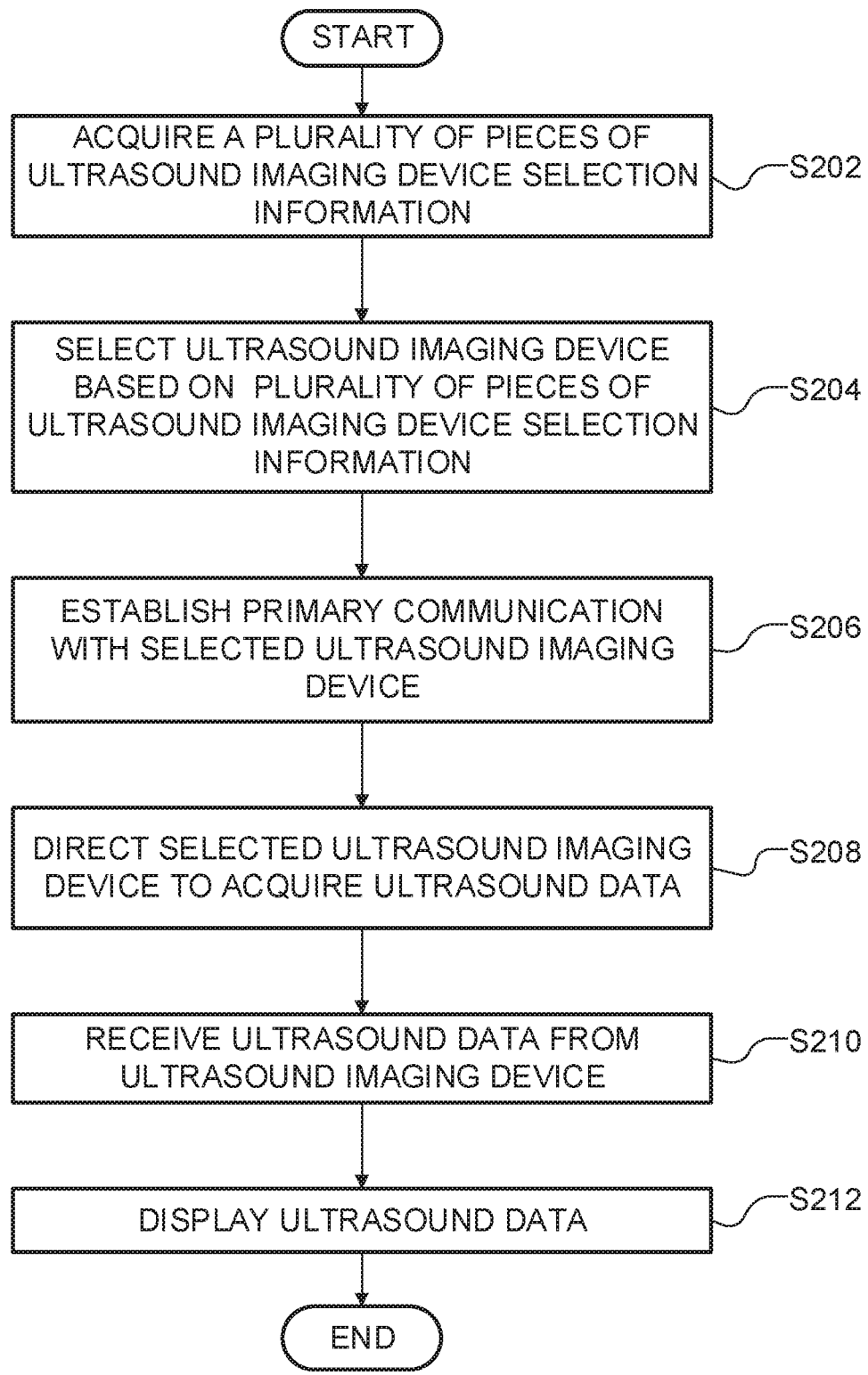
FIG. 2 is a process diagram illustrating an operation of the multi-use electronic display device in the communication method according to an example embodiment of the present disclosure.

FIG. 2 is a flowchart illustrating an operation procedure S200 of the multi-use electronic display device in the communication method according to an embodiment of the present disclosure.

In operation S202, multi-use display device 102 acquires a plurality of pieces of ultrasound imaging device selection information. The plurality of pieces of information may be acquired from one or more ultrasound imaging devices, from the user, or from memory 124.

In order to obtain ultrasound imaging device selection information from one or more ultrasound imaging devices, multi-use display device 102 may search for ultrasound imaging devices 104 that are within range and may establish a preliminary connection with each of them.

In some embodiments, ultrasound imaging devices 104 advertise their presence. For example, communication unit 142 may include a Bluetooth Low Energy module that is configured to periodically advertise the presence of ultrasound imaging device 104. Upon reception of one of these advertisements, multi-use display device 102 may attempt to establish a preliminary connection with ultrasound imaging device 104 in order to request ultrasound imaging device selection information. Alternatively, the advertisements may also contain some or all of the ultrasound imaging device selection information.

As part of the preliminary connection process, multi-use display device 102 and/or ultrasound imaging device 104 may perform an authentication step. An authentication step may involve the exchange of credentials (e.g. username/password or digital certificate information) between multi-use display device 102 and ultrasound imaging device 104. In some embodiments, an authentication server, which may be network-based or cloud-based, mediates the authentication. The authentication step may block further execution of method S200 if the multi-use display device 102 is not authorized to work with the ultrasound imaging device 104 or vice versa.

Ultrasound imaging device selection information received from an ultrasound imaging device 104 may include at least one of identity information of the ultrasound imaging device, function information about the ultrasound imaging device, and status information about the ultrasound imaging device.

The identity information of the ultrasound imaging device may include a universally unique identifier (UUID), a name determined by the manufacturer and/or a user-defined device name. For example, a user-defined device name could be "DrSeymourConvex".

The function information about the ultrasound imaging device may include, for example, one or more of the following: power information (e.g. state of charge of an onboard battery), transducer information, or imaging capabilities. Power information may include power type, such as line or battery or information on the battery. For example, battery information may include type, capacity, state of charge, and/or an estimated life. Transducer information may include the geometry, such as convex or linear, the number of elements, and the number of channels. Imaging capabilities may include available imaging modes such as B-Mode, M-Mode, Color Doppler, Power Doppler, and the like. Transducer information may also include physical features of the probe, such as whether or not a needle guide is present.

The status information about the ultrasound imaging device may include one of the following: connection state, boot state. For example, the connection state may include the presence and/or identity of a different multi-use display device connected to the ultrasound imaging device. The boot state may indicate the power state of the ultrasound imaging device, such as a standby state or an active state.

Multi-use display device 102 may also acquire ultrasound device selection information for ultrasound imaging device 104 based on characteristics of its connection to the ultrasound imaging device 104. For example, the strength of the wireless connection, or an estimate of proximity based at least in part on the strength of the wireless connection.

In some embodiments, ultrasound imaging device 104 may comprise additional sensors to report other status information such as temperature, orientation, or position. For example, an inertial measurement sensor may report the 3D orientation of the probe relative to the ground. In another example, a global positioning sensor may indicate the global position of the ultrasound imaging system.

In some embodiments, the ultrasound device selection information is retrieved from available ultrasound imaging devices 104 in two or more steps. A first step may be used to identify those of ultrasound imaging devices 104 that have a first characteristic. This first characteristic could be a configuration or capability (e.g. transducer type or available imaging modes). Further ultrasound device selection information could then be obtained via the preliminary data connection only for those available ultrasound imaging devices 104 that have the desired characteristic (e.g. only those with curved transducers or only those capable of colour Doppler imaging or only those with at least 50% battery capacity, etc.).

Still referring to operation S202, multi-use display device 102 may acquire ultrasound imaging selection information by receiving an input from the user. For example, the user may request a particular type of exam or a particular time of day they would like to perform an exam. This input may be received through user interface 126 for example by input via a touchscreen or based on voice command.

Multi-use display device 102 may also acquire certain ultrasound imaging device selection information from memory 124. For example, information specifying which ultrasound imaging devices the user is authorized to operate and which ultrasound imaging device was last used by the user may be stored in memory 124.

In operation S204, multi-use display device 102 selects an ultrasound imaging device based on the ultrasound imaging device selection information acquired in operation S202. The selection may be based on an input from the user received through user interface 126 or may be automated.

Multi-use display device 102 may generate and display an ultrasound imaging device list based on the plurality of pieces of ultrasound imaging device selection information. The ultrasound imaging device list may display identifiers (e.g. names, allocated numbers, allocated letters or allocated symbols of the ultrasound imaging devices) that correspond to the ultrasound imaging device, and the plurality of pieces of ultrasound imaging device selection information acquired in operation S202.

The ultrasound imaging device list may be filtered or ranked based on the ultrasound imaging device selection information. For example, if the user has indicated that an abdominal exam is desired, the ultrasound imaging device list may display only ultrasound imaging devices with a transducer geometry suitable for abdominal examinations (e.g. convex). In another example, the ultrasound imaging device list may be ranked by physical proximity. In yet another example, the ultrasound imaging device list may be ranked by estimated battery life. Combinations of these are also possible. One skilled in the art can envision that various criteria could be used and/or combined to match the preference of the user.

Processor 120 may be configured to automate part or all of the selection. For example, if there is only one device on the ultrasound imaging device list, processor 120 may be configured to skip displaying the list to the user and proceed to the next step. Processor 120 may also be configured to automatically select an ultrasound imaging device based on predetermined or user-selectable criteria. For example, processor 120 may preferentially select the ultrasound imaging device that was used in a preceding session.

The ultrasound imaging device list may optionally provide a means for locating or identifying a particular ultrasound imaging device. For example, multi-use display device 102 may receive an input from the user through user interface 126 for one or more of the ultrasound imaging devices on the ultrasound imaging device list. In response to receiving the input, multi-use display device 102 may transmit a page signal to the corresponding ultrasound imaging devices via the preliminary connection. Upon reception of the page signal, the ultrasound imaging device may generate an indication for the user. The indication may include a visible, audible, and/or tactile signal, such as a flashing light, audible tone, or a vibration.

In operation S206, multi-use display device 102 establishes a primary communication channel with the ultrasound imaging device selected in S206.

Operation S206 may involve transmitting information to setup the primary communication channel through the preliminary communication channel. For example, information such as an SSID and a password to setup a WIFI connection may be transmitted through a preliminary Bluetooth connection.

As part of establishing communication to a particular ultrasound imaging device 104, multi-use display device 102 may transmit a signal to the ultrasound imaging device selected in operation S204 to transition it from a standby state to an active state.

Operation S206 may additionally configure multi-use display device 102 to work with the selected ultrasonic imaging device 104. This configuration may involve one or more of:

configuring multi-use display device 102 to perform any steps required to further process for display ultrasound data to be received from the ultrasound imaging device 104;

configuring user interface 126 to provide controls for the various functions of ultrasound imaging device 104. Optionally, only a subset of the available controls which are required for a procedure specified by the ultrasound imaging device selection information are initially displayed on multi-use display device 102;

sizing buffers to accommodate the expected ultrasound imaging data;

configuring user interface 126 to display ultrasound images from the selected ultrasound imaging device 104;

etc.

In operation S208, multi-use display device 102 transmits a control signal to the ultrasound imaging device selected in S204. The control signal may contain commands to set the selected ultrasound imaging device 104 into a particular imaging mode. For example, the commands may control values for a number of imaging parameters that are to be used to acquire ultrasound data. In some embodiments initial values for the imaging parameters are set based on an ultrasound procedure to be performed on a patient. The imaging parameters may comprise parameters that relate to aspects of ultrasound imaging such as the nature of ultrasound signals to be transmitted (e.g. waveform, intensity, aperture, frequency, etc.); the nature of beamforming to be applied to the transmit signals; the nature of beamforming to apply to received ultrasound echo signals; the nature of processing to be applied to received ultrasound signals (e.g. gain, filtering etc.); the nature of an image to acquire (e.g. number of scanlines, depth of scanlines, compounding, etc.).

In operation S210, multi-use display device 102 receives ultrasound data acquired by the ultrasound imaging device in response to the control signal transmitted in operation S208.

In operation S212, multi-use electronic display device 102 displays the ultrasound image data generated in operation S214 via user interface 126.

Additional processing steps may be performed on the ultrasound data on multi-use electronic display device 102 before it is displayed as an image. For example, the ultrasound data may be scan converted.

Figure 3:
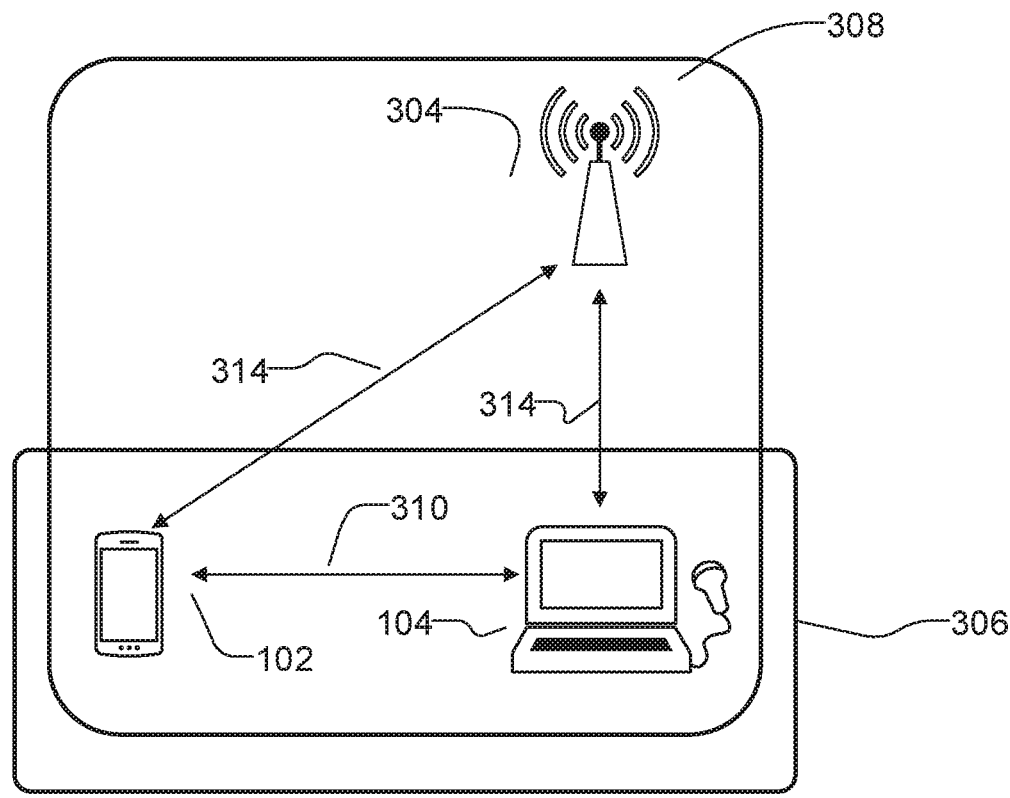
FIG. 3 is a diagram illustrating a preliminary connection between an ultrasound imaging device and multi-use display device and a primary connection via a wireless local area network according to an example embodiment of the present disclosure.

FIG. 3 is a diagram illustrating a preliminary connection between ultrasound imaging device 104 and multi-use display device 102 and a primary connection between the ultrasound imaging device 104 and the multi-use display device 102 via a wireless local area network 308 (e.g., as provided by base station 304). In this embodiment, preliminary connection 310 is a Bluetooth connection and primary connection 314 is a Wi-Fi connection. Multi-use display device 102 establishes Bluetooth connection 310 with ultrasound imaging device 104 within a personal area network 306. Multi-use display device 102 may then transmit configuration information via Bluetooth to ultrasound imaging device 104 in order to establish a Wi-Fi connection 314.

Configuration information to setup Wi-Fi connection 314 may comprise an SSID and a password. This configuration information may be encrypted. Alternatively, configuration information may comprise a reference to previously stored information in ultrasound imaging device memory 144.

In some embodiments, communications between ultrasound imaging apparatus 104 and multi-use display apparatus 102 are encrypted. In some embodiments, encryption is provided by the wireless protocol used for the primary connection. For example, where the primary connection is a Wi-Fi connection, the connection may be secured by WEP or WPA. In some embodiments, to ensure better security, ultrasound imaging device 104 encrypts ultrasound image data using a separate encryption protocol and multi-use display data 102 decrypts the ultrasound image data before displaying it. In such embodiments, information regarding the encryption (such as a public key from multi-use display device 102) may be exchanged by way of the preliminary connection or by way of the primary data connection.

Figure 4:
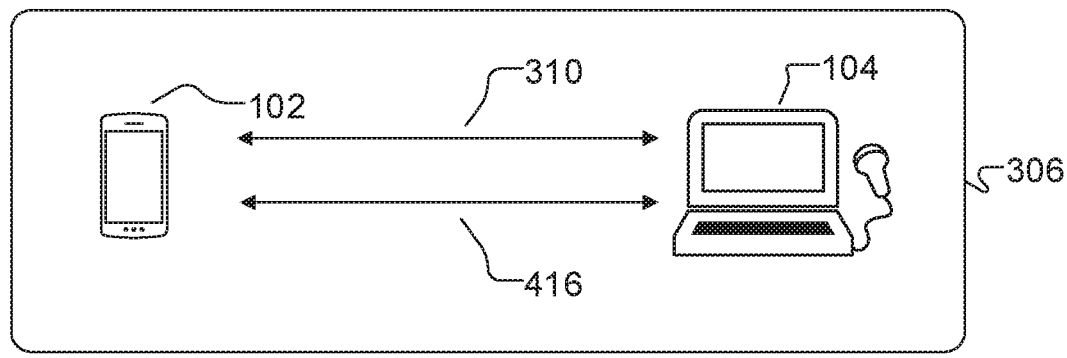
FIG. 4 is a diagram illustrating a preliminary connection between an ultrasound imaging device and multi-use display device and a primary connection via a personal area network according to an example embodiment of the present disclosure.

FIG. 4 is a diagram illustration of a preliminary connection between an ultrasound imaging device and multi-use display device and a primary connection via a personal area network. In this embodiment, preliminary connection 310 is a Bluetooth connection and primary connection 416 is a Wi-Fi direct connection. In a similar fashion, Bluetooth connection 310 is established first, and used to establish Wi-Fi direct connection 416.

Figure 5:
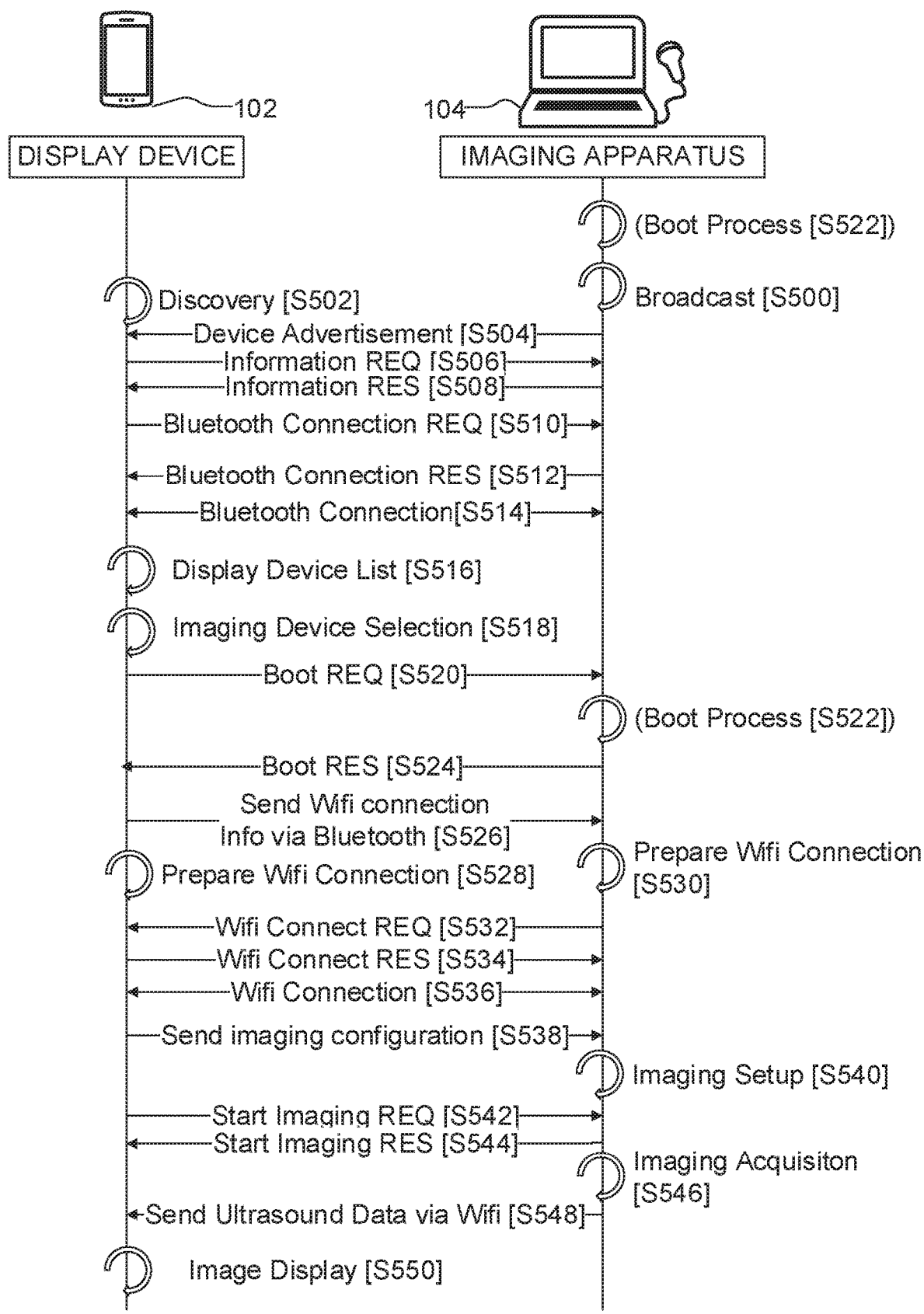
FIG. 5 is a signal flow diagram illustrating signal flows between devices in the communication method according to an example embodiment of the present disclosure.

FIG. 5 is signal flow diagram for an example procedure in which multi-use display 102 selects an ultrasound imaging device 104 and performs wireless communication, according to an embodiment of the present disclosure.

At least one ultrasound imaging device 104 may be in a broadcast state S500, and will periodically send a Bluetooth Device Advertisement signal in operation S504.

In operation S502, multi-use display device 102 initiates a discovery process. If an advertisement signal is received, multi-use display 102 transmits an Information Request signal (Information REQ) at operation S506. Ultrasound imaging device 104 then responds by transmitting an Information Response signal (Information RES) in operation S508.

In operation S510, multi-use display device 102 transmits a Bluetooth Connection Request signal (Bluetooth Connection REQ). If the signal is received, ultrasound imaging device 104 sends multi-use display device 102 a Bluetooth Connection Response signal (Bluetooth Connection RES) at operation S512. Then multi-use display device 102 and ultrasound imaging device 104 establish a Bluetooth communication channel at operation S514.

In operation S516, multi-use display device 102 generates an ultrasound imaging device list from the information acquired during operation S508 from one or more ultrasound imaging devices 104 and displays an ultrasound imaging device list.

In operation S518, multi-use display device 102 select an ultrasound imaging device from the list of ultrasound imaging devices. This selection may be based on an input received from user interface 126.

If the ultrasound imaging device 104 selected in operation S518 is determined to be in a standby state, multi-use display device 102 will send a Boot Request signal (Boot REQ) at operation S520. Ultrasound imaging device 104 then transitions from a standby state to an active state in operation S522. When the boot process is complete, ultrasound imaging device 104 transmits a Boot Response signal (Boot RES) in operation S524.

In operation S526 multi-use display device 102 transmits Wi-Fi connection information via the Bluetooth connection. In operation 528, multi-use display device 102 prepares for a Wi-Fi connection. Similarly, ultrasound imaging devices 104 prepares for Wi-Fi connection in operation S530 and then transmits a Wi-Fi Connection Request signal (Wi-Fi Connect REQ) in operation S532. If multi-use display device 102 receives the WiFi Connection Request signal, multi-use display device 102 transmits a Wi-Fi Connection Response signal (Wi-Fi Connection RES) in operation S534. Afterwards, multi-use display device 102 and ultrasound imaging device 104 establish a Wi-Fi communication channel at operation S536.

Next, in operation S538, multi-use display device 102 transmits imaging configuration information via the Wi-Fi communication channel. If ultrasound imaging devices 104 receives the imaging configuration information, it prepares for imaging at operation S540.

In operation S542, multi-use display device 102 transmits a Start Imaging Request signal (Start Imaging REQ). Ultrasound imaging devices 104 sends a Start Imaging Response signal (Start Imaging RES) in response to the Start Imaging Request signal at operation S544. Then ultrasound imaging devices 104 starts imaging in operation S546. Ultrasound data is sent from ultrasound imaging devices 104 to multi-use display device 102 multi-use display device 102 via the Wi-Fi communication channel in operation S548.

In operation S550, multi-use display device 102 displays the ultrasound data received from ultrasound imaging devices 104. The ultrasound data may be displayed on user interface 126 or on a secondary display.

Figure 6:
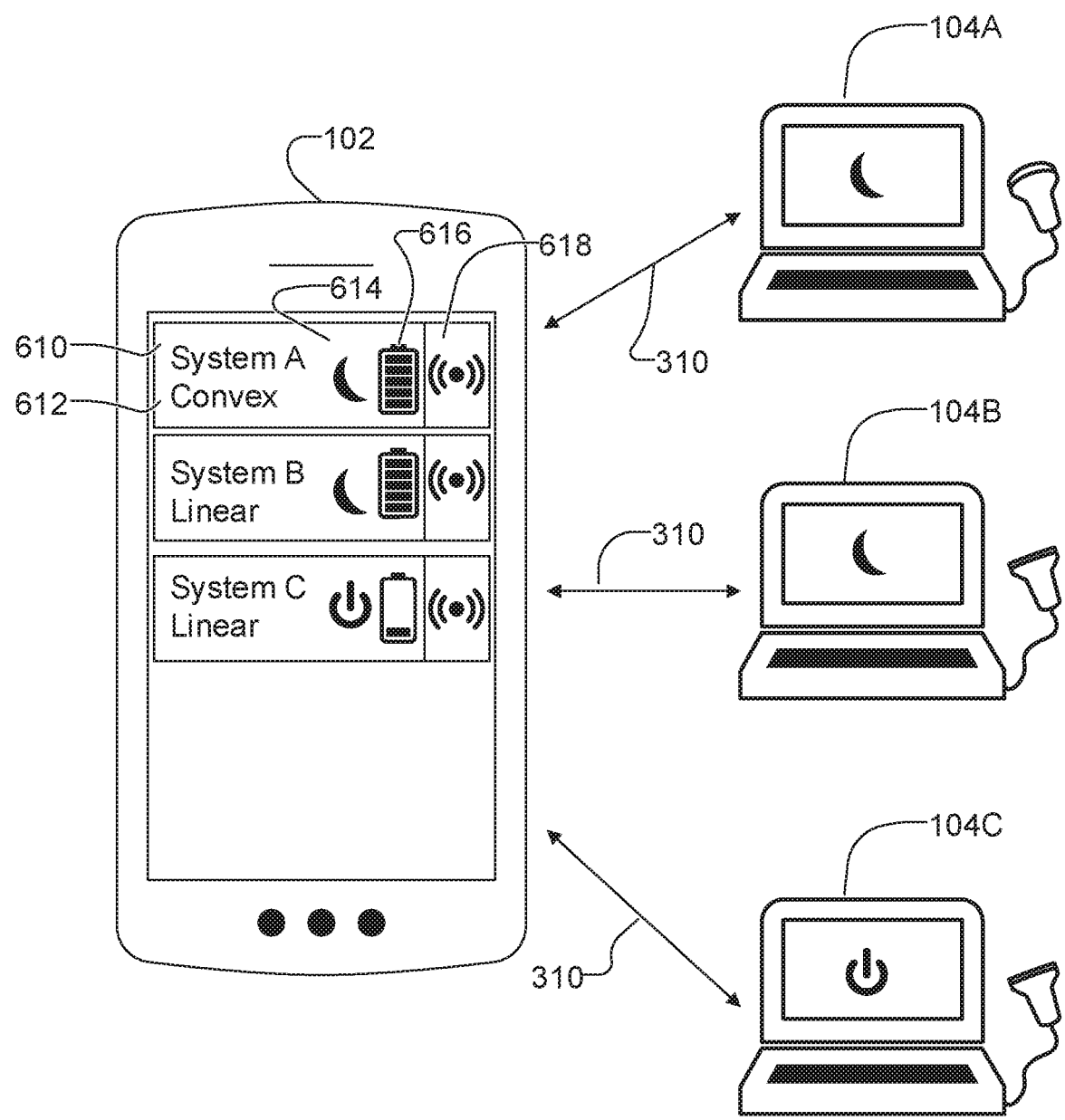
FIG. 6 is an example of a screen shown on the multi-use display device of FIG. 1.

FIG. 6 illustrates an example of a screen that may be shown on multi-use display device 102 during selection operation S204 of FIG. 2. In this example, user interface 126 displays an ultrasound imaging device list comprising an ID indicator 610, a type indicator 612, a state indicator 614, a power indicator 616, and a page control 618 for ultrasound imaging devices 104A-C connected through respective preliminary connections 310. In this example, the ultrasound imaging device list on the user interface shows that System A and System B are in a standby state, while System C is in an active state.

Figure 7:
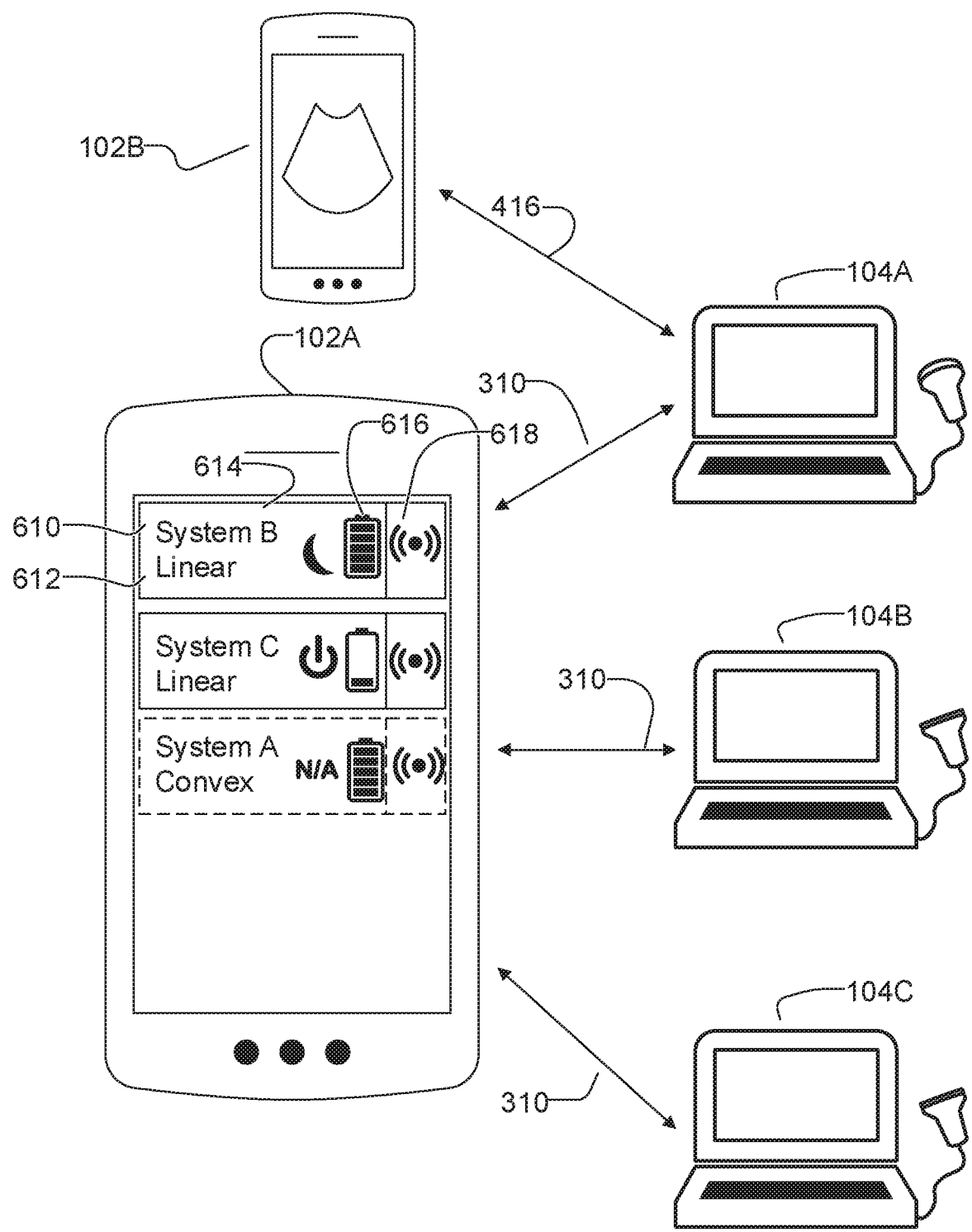
FIG. 7 is an example of a screen shown on multi-use display device of FIG. 1.

FIG. 7 illustrates an example of a screen that may be shown on multi-use display device 102A during selection operation S204 of FIG. 2 in which an ultrasound imaging device 104A is already connected to another multi-use display device 102B via a primary connection 416. In this example, System A 104A is already connected so it is moved to the bottom of the list and marked as unavailable on the user interface.

Figure 8:
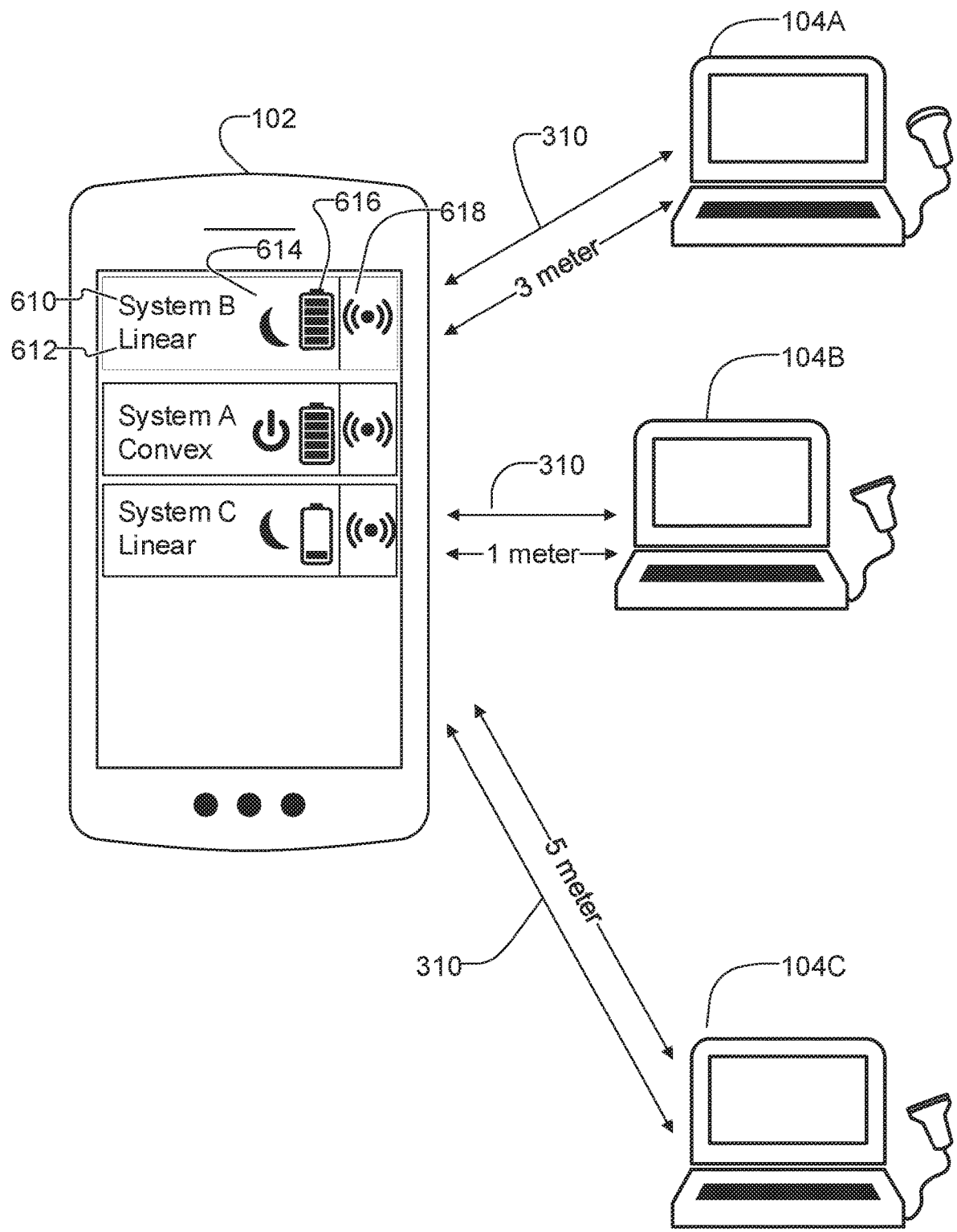
FIG. 8 is an example of a screen shown on multi-use display device of FIG. 1.

FIG. 8 illustrates an example of a screen that may be shown on multi-use display device 102 during selection operation S204 of FIG. 2 in which the ultrasound imaging device list is ranked based on the proximity of the ultrasound imaging devices (connected through preliminary connections 310) to multi-use display device 102. In this example, System B 104B is the ultrasound imaging devices with the strongest signal and is displayed at the top of the list.

Figure 9:
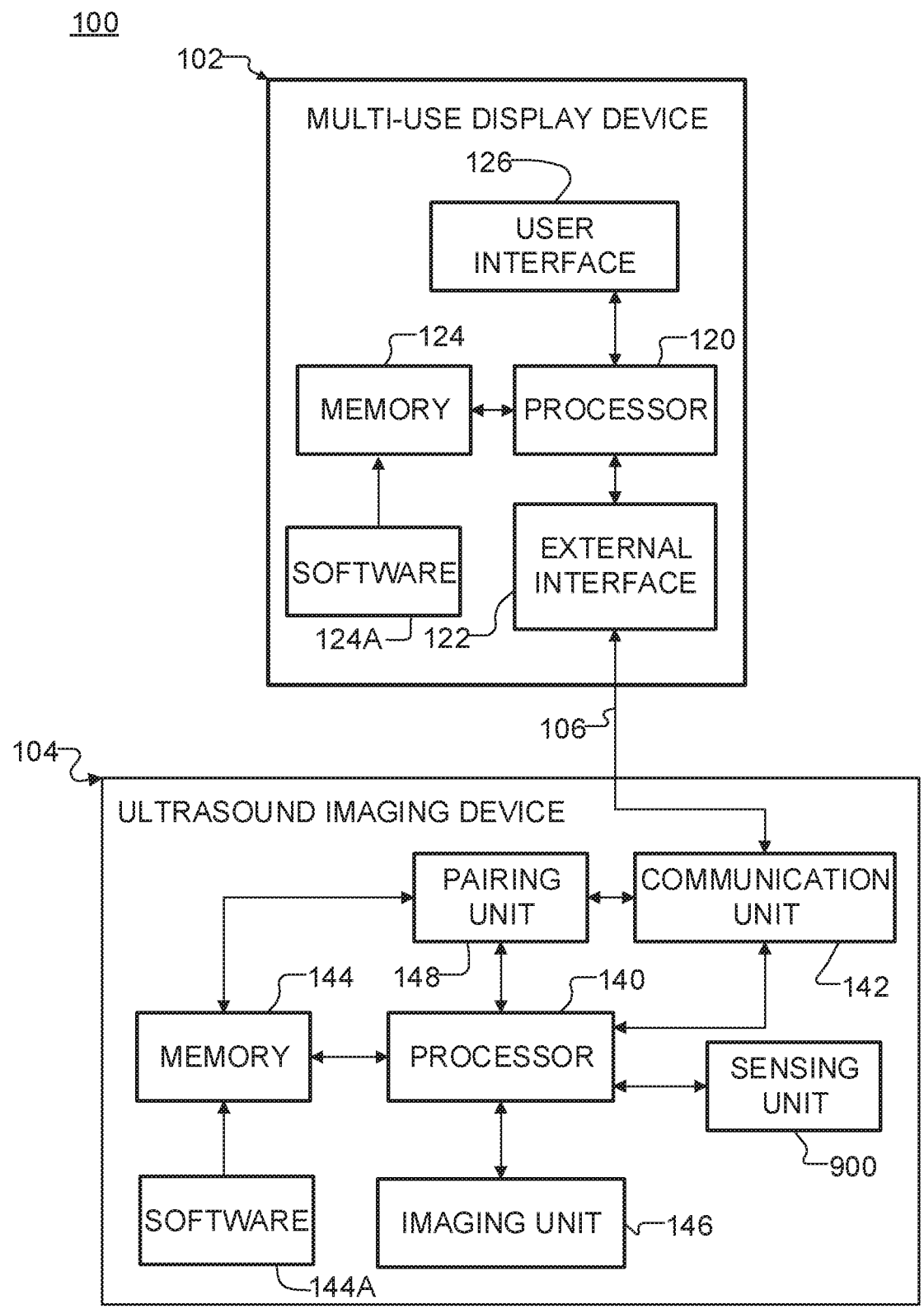
FIG. 9 is schematic diagram of an example embodiment of the ultrasound imaging system.

FIG. 9 illustrates an ultrasound imaging system in accordance with another embodiment of the present disclosure. In this embodiment, ultrasound imaging device 104 further comprises a sensing unit 900 in communication with processor 140. Sensing unit 900 is configured to measure ultrasound imaging device state information.

Sensing unit 900 may also comprise a battery monitor capable of reporting at least one of the following: battery type, state of charge, estimated run-time, battery voltage, battery temperature, battery current.

Sensing unit 900 may also comprise one or more environmental sensors such as an inertial measurement unit, an accelerometer, a compass, a magnetometer, temperature sensor, or a global positioning sensor.

In one embodiment, sensing unit 900 comprises a contact sensor able to sense when ultrasound imaging device 104 is in physical contact with a patient or user. For example, a capacitive touch sensor may sense when the transducer is being held by a user's hand.

An ultrasound imaging system that does not require a display or a user interface can be much more cost effective than traditional ultrasound machines which include dedicated displays and extensive user interfaces.

The simpler and/or partially automated ultrasound imaging device selection process and simplified pairing process as described herein may reduce the time required to start scanning and make the workflow easier.

The ability of a multi-user display device to acquire ultrasound imaging device selection information while the ultrasound imaging device is in a low-power standby state may help reduce power consumption and extend battery life.

In an example use case, an ultrasound department in a hospital has acquired a set of ultrasound imaging devices 104 as described herein. The ultrasound imaging devices 104 are of different types. In this example, some, but not all, of the ultrasound imaging devices 104 incorporate colour Doppler imaging functions. Another difference between the different ultrasound imaging devices 104 is that different ones of the ultrasound imaging devices 104 are equipped with different probes. Some of the ultrasound imaging devices 104 have general purpose linear or convex transducers. Others of the ultrasound imaging devices 104 have special-purpose probes such as probes specialized for transvaginal imaging. Others of the imaging devices may be equipped with hardware features such as guides for conducting needle biopsies. In this use example, the hospital acquired ultrasound imaging devices 104 for a cost significantly less than it would have cost to equip the ultrasound imaging suite with conventional ultrasound imaging machines.

A number of ultrasound technicians work in the hospital. Each of the ultrasound technicians has a tablet computer which runs an ultrasound imaging application. Each of the ultrasound technicians has a full caseload and therefore must be efficient in going about their work. When ultrasound devices 104 are not being used, they are normally stored in a charging dock so that their internal batteries may be kept charged. As different ultrasound imaging devices 104 are used in different amounts during the day, different ultrasound imaging devices 104 may be at different charge levels. These ultrasound imaging devices 104 that have not been used very much or which have been on the charger for a sufficient period of time will be fully charged or nearly fully charged. Others may be partially discharged. Others still may be nearing the end of their battery life.

As each ultrasound technician goes about his or her business, the software on his or her tablet computer causes the tablet computer to interrogate ultrasound imaging devices 104 by way of a preliminary communication channel, such as Bluetooth. Thus, each ultrasound technician's tablet computer has, at any given time, information about the available ultrasound imaging devices 104. When a technician is available to take a new patient, the technician can cause the software to display a list of the available ultrasound imaging devices 104. Those ultrasound imaging devices 104 that are currently in use by somebody else or currently have very low levels of battery charge may be either excluded from the list or marked as being unavailable. The ultrasound technician may select one of the available ultrasound imaging devices 104. The selection causes the ultrasound technician's tablet computer to commence pairing with the selected ultrasound imaging device 104. The pairing may establish a primary data connection such as a Wi-Fi wireless connection. If the selected ultrasound imaging device 104 is not in the place where it should be, or if it is in the midst of one or more other very similar looking ultrasound imaging devices 104, then the technician may, by activating a control on his or her tablet computer, cause the selected ultrasound imaging device 104 to identify itself.

In some cases the ultrasound technician may prepare for selecting an ultrasound device 104 by operating software on the tablet computer to identify a type of ultrasound procedure for which the next patient is scheduled. Information about the type of ultrasound procedure may be retrieved from a patient record or appointment booking system or entered by the technician into the tablet computer. In some cases software running on the tablet computer provides a user interface which allows the user to select from among a number of predefined types of ultrasound examination. In such embodiments the selection step may include identifying those of available ultrasound imaging devices 104 that are suitable for the selected type of ultrasound examination. The software may suppress display of those ultrasound imaging devices 104 that are not suitable for the selected type of ultrasound examination or in some other manner indicate their non-suitability.

Software on the multi-use display device determines an initial set of imaging parameters to be used by the selected ultrasound imaging device. This initial set of imaging parameters may be predefined and associated with a selected predefined type of ultrasound examination. In some embodiments the imaging parameters are transmitted to the selected ultrasound imaging device before the ultrasound imaging device is initialized (e.g. booted) and an initialization sequence of the ultrasound imaging device configures the ultrasound imaging device according to the imaging parameters while the ultrasound imaging device is being initialized such that the ultrasound imaging device is already configured according to the imaging parameters as soon as it has completed its initialization (e.g. as soon as it is booted up).

Having identified and taken the selected ultrasound imaging device 104, the technician proceeds to perform the desired ultrasound examination of the patient. By the time the ultrasound technician has reached the patient's bedside, the pairing process has been completed, the ultrasound imaging device has been configured with imaging parameters suitable for the type of ultrasound examination to be performed and so ultrasound examination can proceed without delay. Ultrasound data from the ultrasound imaging device 104 is provided to the technician's tablet computer. Ultrasound images may be stored on the tablet computer and/or uploaded to a server to be reviewed by a radiologist and/or stored in a medical record.

When the technician is done with the ultrasound imaging device 104, the technician may unpair the ultrasound imaging device with his or her tablet computer, for example, by activating a control on the tablet computer and may return the ultrasound imaging device to a charging station for later use.

In some embodiments, an ultrasound technician may know that he or she will need to use a particular ultrasound imaging apparatus 104 in a short while. Some embodiments permit the user to reserve the ultrasound imaging device by inputting a command on his or her computer. The tablet computer may confirm the reservation to the ultrasound imaging device, for example, by way of the preliminary communication link. The ultrasound imaging device itself may record the reservation request and start a countdown timer for a reservation time. For example, the system may be set up to allow ultrasound technicians to reserve ultrasound imaging devices 15 minutes in advance only. When such a reservation has been made, the ultrasound imaging device 104 may communicate the reservation information to other multi-use display devices 102 (e.g. the tablet computers of other technicians) such that the other technicians can see that the particular ultrasound imaging device 104 has been reserved and optionally by whom. These communications are made by way of the preliminary data connection in some embodiments.

Although it is not mandatory, it is convenient that multi-use display devices 102 may be provided by standard off-the-shelf hardware such as smart phones or tablet computers which are customized by the addition of application software having functions for interacting with ultrasound imaging devices 104 and displaying ultrasound images as described herein. It is also convenient and cost effective but not mandatory for ultrasound imaging devices 104 to have no user interface or only minimal user interfaces.

While the above description contains many specifications, these should not be construed as limitations on the scope of any embodiment, but as exemplifications of various embodiments thereof. Many other ramifications and variations are possible within the teachings of the various embodiments.

Thus the scope should be determined by the appended claims and their legal equivalents, and not by the examples given.

INTERPRETATION OF TERMS

Unless the context clearly requires otherwise, throughout the description and the claims:
  "comprise", "comprising", and the like are to be construed in an inclusive sense, as opposed to an exclusive or exhaustive sense; that is to say, in the sense of "including, but not limited to";
  "connected", "coupled", or any variant thereof, means any connection or coupling, either direct or indirect, between two or more elements; the coupling or connection between the elements can be physical, logical, or a combination thereof;
  "herein", "above", "below", and words of similar import, when used to describe this specification, shall refer to this specification as a whole, and not to any particular portions of this specification;
  "or", in reference to a list of two or more items, covers all of the following interpretations of the word: any of the items in the list, all of the items in the list, and any combination of the items in the list;
  the singular forms "a", "an", and "the" also include the meaning of any appropriate plural forms.
  Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs")). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

While processes or blocks are presented in a given order, alternative examples may perform routines having steps, or employ systems having blocks, in a different order, and some processes or blocks may be deleted, moved, added, subdivided, combined, and/or modified to provide alternative or sub-combinations. Each of these processes or blocks may be implemented in a variety of different ways. Also, while processes or blocks are at times shown as being performed in series, these processes or blocks may instead be performed in parallel, or may be performed at different times.

In addition, while elements are at times shown as being performed sequentially, they may instead be performed simultaneously or in different sequences. It is therefore intended that the following claims are interpreted to include all such variations as are within their intended scope.

Certain aspects of the invention may also be provided in the form of a program product. The program product may comprise any non-transitory medium which carries a set of computer-readable instructions which, when executed by a data processor, cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

In some embodiments, some aspects of the invention may be implemented in software. For greater clarity, "software" includes any instructions executed on a processor, and may include (but is not limited to) firmware, resident software, microcode, and the like. Both processing hardware and software may be centralized or distributed (or a combination thereof), in whole or in part, as known to those skilled in the art. For example, software and other modules may be accessible via local memory, via a network, via a browser or other application in a distributed computing context, or via other means suitable for the purposes described above.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

What is claimed is:

1. A method of locating an ultrasound imaging device comprising:
    a multi-use electronic display device acquiring imaging device selection information from each of one or more ultrasound imaging devices capable of transmitting and receiving ultrasound energy;
    the multi-use electronic display device displaying the image device selection information of each of the one or more ultrasound imaging devices, wherein when displaying the respective image device selection information, the multi-use electronic display device further displays a page user-interface control for each of the one or more ultrasound imaging devices;
    the multi-use electronic display device receiving input that activates the page user-interface control for a selected ultrasound imaging device of the one or more ultrasound imaging devices; and
    the multi-use electronic display device transmitting a page signal to the selected ultrasound imaging device, wherein upon receipt of the page signal, the selected ultrasound imaging device generates an indication.

2. The method of claim 1, further comprising the multi-use electronic display device establishing a primary wireless communication link with the selected ultrasound imaging device.

3. The method of claim 1, wherein the imaging device selection information is acquired using a first wireless communication protocol, and the page signal is transmitted using the same first wireless communication protocol.

4. The method of claim 2, further comprising the multi-use electronic display device establishing a primary wireless communication link with the selected ultrasound imaging device, and the establishing is performed according to a second wireless communication protocol different from the first wireless communication protocol.

5. The method of claim 1, wherein when the ultrasound imaging device generates the indication, the ultrasound imaging device generates a visible signal.

6. The method of claim 5, wherein the visible signal comprises a flashing light.

7. The method of claim 1, wherein when the ultrasound imaging device generates the indication, the ultrasound imaging device generates an audible signal.

8. The method of claim 7, wherein the audible signal comprises an audible tone.

9. The method of claim 1, wherein when the ultrasound imaging device generates the indication, the ultrasound imaging device generates a tactile signal.

10. The method of claim 9, wherein the tactile signal comprises a vibration.

11. An ultrasound imaging system comprising:
    one or more ultrasound imaging devices capable of transmitting and receiving ultrasound energy; and
    a multi-use electronic display device configured to:
        acquire imaging device selection information from each of the one or more ultrasound imaging devices capable of transmitting and receiving ultrasound energy;
        display the image device selection information of each of the one or more ultrasound imaging devices, wherein when displaying the respective image device selection information, the multi-use electronic display device further displays a page user-interface control for each of the one or more ultrasound imaging devices;
        receive input that activates the page user-interface control for a selected ultrasound imaging device of the one or more ultrasound imaging devices; and
        transmit a page signal to the selected ultrasound imaging device, wherein upon receipt of the page signal, the selected ultrasound imaging device generates an indication.

12. The system of claim 11, wherein the multi-use electronic display device is further configured to establish a primary wireless communication link with the selected ultrasound imaging device.

13. The system of claim 11, wherein the imaging device selection information is acquired using a first wireless communication protocol, and the page signal is transmitted using the same first wireless communication protocol.

14. The system of claim 13, wherein the multi-use electronic display device is further configured to establish a primary wireless communication link with the selected ultrasound imaging device, and the establishing is performed according to a second wireless communication protocol different from the first wireless communication protocol.

15. The system of claim 11, wherein when the ultrasound imaging device generates the indication, the ultrasound imaging device generates a visible signal.

16. The system of claim 11, wherein when the ultrasound imaging device generates the indication, the ultrasound imaging device generates an audible signal.

17. The system of claim 11, wherein when the ultrasound imaging device generates the indication, the ultrasound imaging device generates a tactile signal.

18. A non-transitory computer readable medium storing instructions for performing a method of locating an ultrasound imaging device, wherein when the instructions are executed by one or more processors of a multi-use electronic display device, the one or more processors are configured to:
- acquire imaging device selection information from each of one or more ultrasound imaging devices capable of transmitting and receiving ultrasound energy;
- display the image device selection information of each of the one or more ultrasound imaging devices, wherein when displaying the respective image device selection information, the multi-use electronic display device further displays a page user-interface control for each of the one or more ultrasound imaging devices;
- receive input that activates the page user-interface control for a selected ultrasound imaging device of the one or more ultrasound imaging devices; and
- transmit a page signal to the selected ultrasound imaging device, wherein upon receipt of the page signal, the selected ultrasound imaging device generates an indication.

19. The medium of claim 18, wherein the multi-use electronic display device is further configured to establish a primary wireless communication link with the selected ultrasound imaging device.

20. The medium of claim 18, wherein the imaging device selection information is acquired using a first wireless communication protocol, and the page signal is transmitted using the same first wireless communication protocol.

* * * * *